(12) United States Patent
Broermann et al.

(10) Patent No.: US 6,980,304 B2
(45) Date of Patent: Dec. 27, 2005

(54) METHOD FOR MEASURING A CHARACTERISTIC DIMENSION OF AT LEAST ONE PATTERN ON A DISC-SHAPED OBJECT IN A MEASURING INSTRUMENT

(75) Inventors: Oliver Broermann, Dresden (DE); Diana Mattiza, Dresden (DE); Sebastian Schmidt, Dresden (DE)

(73) Assignee: Infineon Technologies, AG, Munich (DE)

( * ) Notice: Subject to any disclaimer, the term of this patent is extended or adjusted under 35 U.S.C. 154(b) by 0 days.

(21) Appl. No.: 10/802,728

(22) Filed: Mar. 18, 2004

(65) Prior Publication Data

US 2004/0201858 A1 Oct. 14, 2004

Related U.S. Application Data

(63) Continuation of application No. PCT/DE02/03492, filed on Sep. 17, 2002.

(30) Foreign Application Priority Data

Sep. 28, 2001 (DE) ............................. 101 47 880

(51) Int. Cl.⁷ ............................................ G01B 11/02
(52) U.S. Cl. ................................................... 356/625
(58) Field of Search .............................. 356/625–636, 356/399–401; 250/548, 201.6; 702/94

(56) References Cited

U.S. PATENT DOCUMENTS

| | | | |
|---|---|---|---|
| 5,648,854 A | 7/1997 | McCoy et al. | |
| 6,323,953 B1 | 11/2001 | Blaesing-Bangert et al. | |
| 6,399,409 B2 | 6/2002 | Sasaki et al. | |
| 6,768,958 B2 * | 7/2004 | Ivanovic et al. | 702/94 |
| 6,897,422 B2 * | 5/2005 | Broermann | 250/201.6 |

FOREIGN PATENT DOCUMENTS

EP     0 973 068 A3     1/2000

* cited by examiner

*Primary Examiner*—Hoa Q. Pham
(74) *Attorney, Agent, or Firm*—Edell, Shapiro & Finnan, LLC

(57) ABSTRACT

The measurement of the width of a pattern on a semiconductor wafer or a flat panel is carried out in an optical microscope or a scanning electron microscope in a number of measuring steps. By a computing rule, the quality of the correlation between the measured data obtained in the individual measurement steps, as well as reference data taken from the design, the value for the parameter is calculated and compared with a limiting value obtained from experience. In the event of violation of the limiting value, a signal is generated and the further processing of the object is interrupted.

14 Claims, 2 Drawing Sheets

METHOD FOR MEASURING A CHARACTERISTIC DIMENSION OF AT LEAST ONE PATTERN ON A DISC-SHAPED OBJECT IN A MEASURING INSTRUMENT

CROSS REFERENCE TO RELATED APPLICATIONS

This application is a continuation of PCT Application No. PCT/DE02/03492, filed on Sep. 17, 2002, and titled "Method for Measuring a Characteristic Dimension of at Least One Pattern on a Disc-Shaped Object in a Measuring Instrument," which claims priority from German Patent Application No. DE 10147880.1, filed on Sep. 28, 2001, and titled "Method for Measuring a Characteristic Dimension of at Least One Pattern on a Disc-Shaped Object in a Measuring Instrument," the entire contents of which are hereby incorporated by reference.

FIELD OF THE INVENTION

The present invention relates to a method for measuring a characteristic dimension of at least one pattern on a disc-shaped object in a measuring instrument having a computing and control unit.

BACKGROUND

The proportion of outlay on quality assurance is gaining in importance given the continuously reducing pattern sizes on semiconductor products, as also in the field of flat panel displays. In general, for a product consisting of many planes, a measurement of test structures or component structures is carried out at least for each lithographically patterned plane, followed by comparison with desired or reference limiting values.

The corresponding measurements can be carried out with reference to absolute positional accuracy (registration), relative positional accuracy (overlay), layer thickness or pattern height, pattern width or pattern length, pattern edge angle, etc. An important subgroup of these measured data, which corresponds to a distance measurement between two points on the surface of a wafer slice, a mask, a flat panel display, etc., is denoted as CD (Critical Dimension) measurement. Because the optical resolution limit is being reached due to the continuously reducing pattern sizes, increasing use is also being made of scanning electron microscopes (SEMs) instead of photooptical measuring instruments. Such a CD measurement for determining the characteristic dimensions, for example, of predefined patterns such as lines, rectangles, slits, etc., can validate the quality of a preceding lithographic step.

A series of aligning and measuring steps are generally carried out in order to perform the CD measurement in an optical or scanning electron microscope. A sequence of such measuring steps is illustrated schematically, for example in FIG. 1. After lithographic patterning has been carried out in a lithography cluster including resist coating, hot and cool plates, exposing the resist, cooling down, developing and hardening, as well as cleaning, etc. The first step, in this case, is to carry out an overlay measurement to check the accuracy of the alignment of the currently patterned plane with reference to preceding planes. Such measurements are usually accomplished in measuring instruments specifically set up therefore.

After the overlay measurement, the product to be measured, for example, a semiconductor wafer, is transferred to the CD measuring instrument, in which the semiconductor wafer is aligned on a stage, i.e., a substrate holder. A first measuring step includes a global alignment. In this measuring step, alignment marks set up specifically for this purpose are used to align the stage with the wafer into a defined co-ordinate position relative to the optical or electronic lens system.

The stage with the wafer is positioned by positional data taken from the pattern design such that the structure to be measured passes roughly into the raster image field of the lens system. With digital image processing, the targeted pattern is detected in this image field by pattern recognition methods, and the semiconductor wafer is subsequently readjusted.

In a further step, the lens system is aligned such that as high as possible a resolution or sharp definition is achieved for the imaging. Like the step of pattern recognition, this step, known as autofocus, is sufficiently well known from the prior art to the average person skilled in the art. Autofocus steps can be implemented in the case of optical microscopes by varying lens separations, and in the case of scanning electron microscopes, by varied current intensities or induction intensities in the lens coils.

A further measuring step, which relates chiefly to scanning electron microscopes, is the checking of the stigmation quality, i.e., the astigmatism. In this case, the setting values, determined from a first measuring curve in a first direction, for example, "X", for the focus are compared with those of a second one, in a second direction, for example, "Y", orthogonal to the first direction. Depending on a result to be achieved, which is a function of the pattern design to be imaged, the lens system can be readjusted here once more.

Only after this step does the actual CD measurement take place, for example, by selecting two opposite edge points for the purpose of measuring the width of a pattern as characteristic dimension, and measuring their spacing.

The measured value of the pattern width is then fixed as CD value for this pattern and, if appropriate, compared, by averaging together with further pattern width measurements, to a tolerance band, prescribed from the design rule, for CD values. When the limits of this tolerance band are exceeded, the semiconductor wafer must be passed on for reworking in the normal case after the lithography step.

The subsequent process step, in this case, an etching step, can be carried out when the tolerance limits are observed.

Whereas in past years the measuring accuracy of the scanning electron microscopes has sufficed completely for distinguishing different dimensions of patterns within a prescribed tolerance band, this is becoming more difficult nowadays with the continuously decreasing pattern sizes. For example, a typical 10% tolerance band of a 150 nm wide gate stack of a transistor, for example, of a memory product, is 15 nm. Consequently, an accuracy of 3 nm is to be achieved by the scanning electron microscope given the requirement of a 20% resolution within this tolerance.

SUMMARY

The present invention can check and/or improve the quality of a CD measurement in an optical or scanning electron microscope.

A method for measuring a characteristic dimension of at least one pattern on a disc-shaped object in a measuring instrument having a lens system and a computing and control unit can include measuring at least one alignment mark for aligning the provided disc-shaped object relative to the lens system of the measuring instrument, measuring the at least one pattern in order to detect the at least one pattern on the disc-shaped object, measuring the at least one pattern in order to set the lens system to achieve a sharp image of the at least one pattern, and measuring the characteristic dimension of the at least one pattern. Then at least one pattern can be formed in at least one fabrication step and can subsequently be checked by the measurement. At least one of the measuring steps can be assigned, in each case, a parameter and a computing rule for determining a value for the parameter. The parameter represents the quality of a measuring step carried out such that a limiting value can be assigned to the parameter, the computing and control unit can apply the computing rule to calculate the value of the parameter from the measured data obtained in the at least one measuring step, the computing and control unit can compare the calculated value with the limiting value, and at least one of the fabrication steps to form the pattern can be repeated for the disc-shaped object in the event of overshooting of at least one of the limiting values.

In accordance with the present invention, the quality of CD measurements can be improved by subjecting the measuring steps, which are taken to prepare for the actual CD measurement to quality control, individually or in their totality. The measuring steps frequent automatically carried out operations were performed with incorrectly selected patterns in the fabrication or that the algorithms used led to carrying out the step inaccurately. Although the actual CD measurement can be carried out with high accuracy, the possible microscope settings may then be defective in some circumstances, and therefore, lead to an inaccurate CD measurement. In the customary case, this can lead to an indication that reworking may be necessary, although the object is actually in the tolerance band, or vice versa.

This faulty behavior can be prevented by checking the individual measuring steps. Introduced for this purpose is a parameter, which leads by a computing rule to an unique assignment to the measurement result of the measuring step respectively carried out. Present in the normal case for the individual measuring steps are reference data which are present, for example, in a reference image of the patterns or alignment marks or in the form of ideal measuring curves. The measured data can then be compared with these reference data, the quality of the correspondence between measured data and reference data being transferred by the computing rule into the parameter value. Ideally, the parameter can include a number range with an adequate fineness of subdivisions. In particular, there can be a unique relationship between the quality determined from the comparison and the parameter value.

The corresponding calculations can be carried out by the computing and control unit of the measuring instrument, i.e., either a scanning electron microscope or an optical microscope. By analogy with the validation of a CD measurement with reference to the observance of a tolerance band, according to the invention, a comparison with limiting values obtained and/or fixed from experience and valid individually for each parameter can be carried out for each parameter value in order to delimit a tolerance band. If such a limiting value is violated, a warning signal can be generated, which indicates that a measuring step carried out defectively. As a result, this signal can, for example, prompt the repetition of this measuring step or, for example, cause a supervisor to carry out the same measuring step with other instrument settings such that the source of error is eliminated, if appropriate. A simple example would be an incorrectly selected alignment mark or pattern. The supervisor would, at the behest of the signal, can search for and set the originally desired mark.

At the behest of the generated warning signal, the supervisor can establish, however, that the error cannot be carried out because of the defective quality of the nature of the pattern itself, and so it is possible to find sources of error in process steps either in the individual case or with statistical methods from an evaluation of the parameter values according to the invention. The error analysis can be improved in the case of semiconductor fabrication. In an embodiment, the parameter values, calculated according to the invention, of the individual measuring steps and relating to each object can be stored in a database, which is coupled to the computing and control unit. Analysis algorithms can directly access these data later.

According to the invention, the processing of a disc-shaped object, i.e., a mask, a reticule, a semiconductor wafer, a flat panel display, or similar objects, can be stopped when an individually set limiting value is violated by one of the parameter values. Since it would be possible for the actual CD measurement to determine a CD value which lies within the tolerance band given by the specification of the object, a defective object can pass the quality control unimpeded in accordance with the prior art, while not possible given defective performance in the preceding measuring steps. It is likewise possible for a CD value deviating relatively widely from the tolerance to be implied by the high effect of errors in the preceding measuring steps, although the lithographic patterning could have proceeded to specification. Such misjudgements can be prevented according to the invention, which can lead to a higher measuring accuracy, and thus even to a higher throughput in the lithographic step.

BRIEF DESCRIPTION OF THE DRAWINGS

The invention is now to be explained in more detail with the aid of exemplary embodiments together with the figures of a drawing, in which.

DETAILED DESCRIPTION

Figure 1:
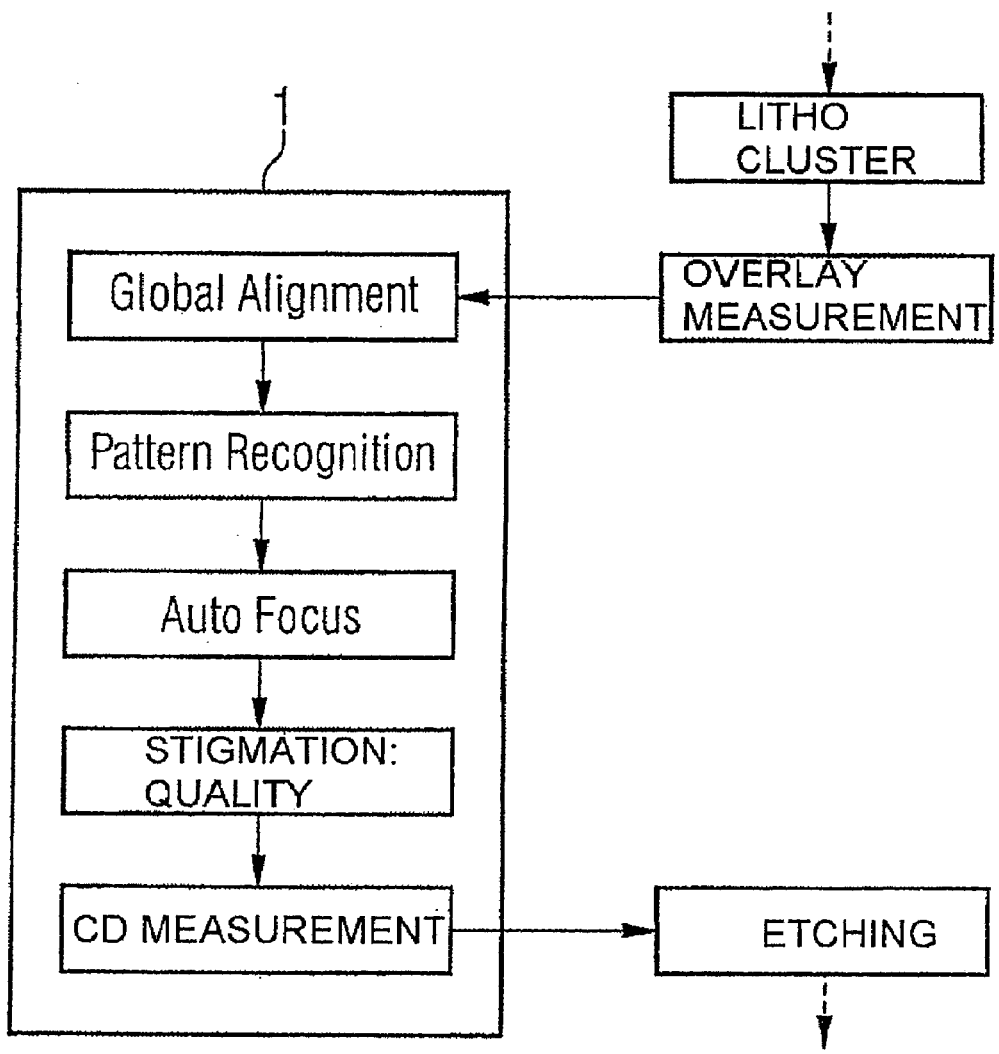
FIG. 1 shows a flowchart of the measuring steps in a CD measuring instrument in accordance with the prior art.
Figure 2:
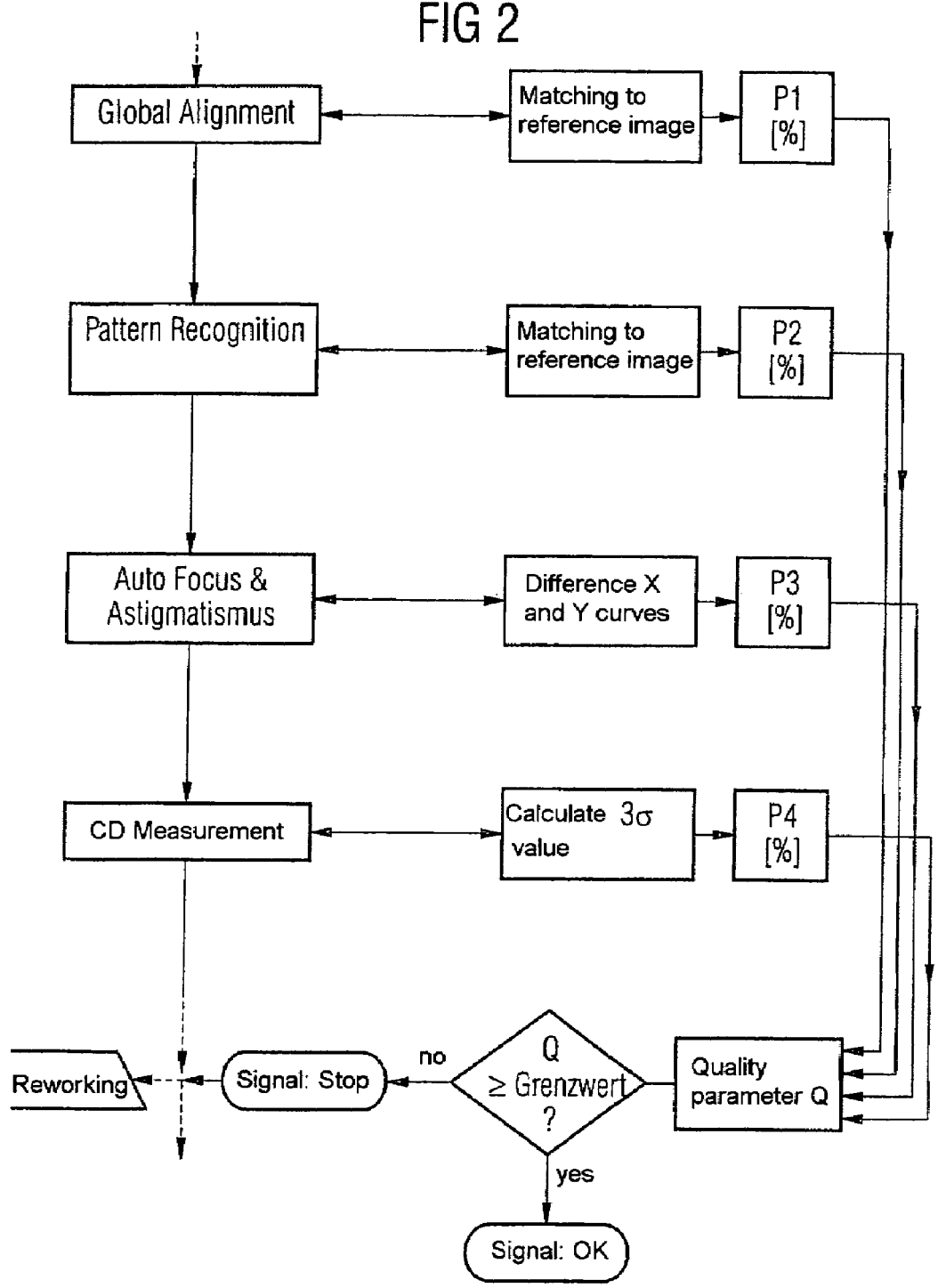
FIG. 2 shows an example according to the invention for the purpose of determining a quality parameter for verifying the quality of a CD measurement.

FIG. 2 shows the measuring steps, illustrated in FIG. 1, for carrying out a CD measurement in a scanning electron microscope 1 in a flow sequence on the left-hand side, as well as, in a fashion assigned thereto in the middle by way of illustration, the form in which the measured data obtained in the respective step are present. As already described, the process can start by carrying out an aligning step, i.e., the global alignment. The location of the alignment mark can be sought and the image of the alignment mark can be compared with a reference image, obtained from the pattern design, of the alignment mark. In a correlation method, the two images can be brought to optimal correspondence, as a result of which an assignment is achieved between the coordinates of the wafer stage and the coordinates of the design data. The optimal correlation or the quality of the correspondence can be transferred uniquely via a previously stipulated computing rule to a parameter value P1, which is present in this exemplary embodiment in the unit of percentages, with the extreme values of 0% for lack of correspondence, 100% for complete correspondence, and a limiting value of 90% which can be obtained from experience for correctly found and adequately clearly visible alignment marks.

Using the known coordinates of the patterns to be examined, it is possible to approach an environment of these patterns with the aid of the wafer stage. In the present exemplary embodiment, this is a memory product, more precisely, the trench capacitor plane, as may be gathered from the middle sketch in FIG. 2. The spacing, as well as the length and width of three trench capacitors, can be examined in the CD measurement. A pattern recognition algorithm for detecting the pattern can be present on the digital image, obtained in this measuring step, of the pattern environment owing to the pattern geometry known from the design data and to the coarse coordinate stipulation. In the sketch of FIG. 2, it is important, for example, that the spacing of a pair of trench capacitors is selected for measurement when determining the spacing, and not the diagonal spacing between two pairs of trench capacitors. The comparison with the reference image from the design data likewise yields an optimal relationship or quality of the correspondence, which is converted into a second parameter P2 by a second computing rule. Like the parameter P1, this parameter is also specified in percentages, and therefore, has, as a lower limit, the value 0% for a pattern not found, and 100% for a pattern identified as completely identical, i.e., a trench capacitor. Here, as well, 90% which was obtained from experience can be fixed as limiting value.

In this example, the measurement signal strengths obtained in an X-direction and the Y-direction orthogonal thereto can be correlated with one another in the autofocus measurement. Resulting therefrom is a measure of the astigmatism of the electromagnetic lenses. The computing and control unit of the scanning electron microscope 1 can use a further computing rule to calculate in turn from the differential signal a parameter P3, which corresponds to the quality of the correspondence and can be likewise given in percentages. Once again, 100% signifies maximal correspondence, i.e., absence of astigmatism, while 0% indicates uncorrelated signals. The unique function corresponding to the computing rule can reflect for the limiting value of 90% a value, which can still just be borne for the astigmatism of the electromagnetic lenses.

In the measuring step of the CD measurement itself, the measurement can be repeated at least three times so that a further parameter P4 can be calculated by a further computing rule. The parameter P4 can be uniquely related to the 3-$\sigma$ deviations from the mean value calculated from the repeated CD measurements on the one pattern. The spread of repeated CD measurements on one and the same pattern can reflect either instrument-dependent measuring inaccuracies themselves, or diffuse properties of the pattern. The value of 100% for the parameter P4 can correspond to a completely reproducible CD measurement of its value, while 0% indicates that the standard deviation can correspond to the pattern width itself. The limiting value can be assumed to be 90% in the case of a non-linear relationship between the 3-sigma value and the parameter P4.

The parameters P1–P4 can be stored for each object in a database. The parameters can be required later when the quality parameter Q determined from them itself again violates a further limiting value, which has been obtained from experience. The parameter Q can be calculated in the exemplary embodiment by multiplying the parameters P1 to P4 and subsequently normalizing them back into the percentage band by the computing and control unit. For an object, i.e., in the exemplary embodiment a semiconductor wafer patterned previously in a lithographic step with a trench capacitor plane, the parameters were determined as P1 equals 92%, P2 equals 98%, P3 equals 91% and P4 equals 99%. The limiting value, obtained by experience, for the quality parameter Q, can be 80%. It follows from Q equals P1×P2×P3×P4 equals 81.23% that the tolerance band for the quality of the CD measurement was observed. A signal can be generated which communicates this result to the supervisor on a display screen.

If, by contrast, the limiting value of 80% had been undershot, the further processing of this semiconductor wafer would have been stopped. The first step then would have been to take the individual parameters P1 to P4 from the entered database values and to investigate them in order to limit the possible source of error. If it emerges from this that the pattern quality of the alignment mark or the inspected structure itself is defective, the relevant semiconductor wafer is sent for reworking, for example.

Since 213.1 nm has been measured in the present case for the width of the trench capacitor, and the tolerance band is 210 plus/minus 20 nanometers, the semiconductor wafer can be handed over in this exemplary embodiment to the further process step for etching.

While the invention has been described in detail and with reference to specific embodiments thereof, it will be apparent to one skilled in the art that various changes and modifications can be made therein without departing from the spirit and scope thereof. Accordingly, it is intended that the present invention covers the modifications and variations of this invention provided they come within the scope of the appended claims and their equivalents.

LIST OF REFERENCE SYMBOLS

1 Microscope, scanning electron microscope
P1 Parameter for global alignment
P2 Parameter for pattern recognition
P3 Parameter for astigmatism
P4 Parameter for spreading in the case of repeated CD measurement
Q Combined quality parameter

We claim:
1. A method for measuring a characteristic dimension of at least one pattern on a disc-shaped object in a measuring instrument, the measurement instrument having a lens system and a computing and control unit, the at least one pattern being formed in at least one fabrication step and subsequently being checked by the measurement, comprising:
measuring at least one alignment mark for aligning the provided disc-shaped object relative to the lens system of the measuring instrument;
measuring the at least one pattern in order to detect the at least one pattern on the disc-shaped object;
measuring the at least one pattern in order to set the lens system to achieve a sharp image of the at least one pattern; and
measuring the characteristic dimension of the at least one pattern, wherein at least one of the measuring steps is assigned in each case a parameter and in each case a computing rule for determining a value for the parameter, which represents the quality of the measuring step respectively carried out, a limiting value is assigned to the parameter, the computing and control unit applies the computing rule to calculate the value of the parameter from the measured data obtained in the at least one measuring step, the computing and control unit com- pares the calculated value of the parameter with the assigned limiting value, and at least one of the fabrication steps required to form the pattern is repeated for the disc-shaped object in the event of overshooting of at least one of the limiting values.

2. The method according to claim 1, wherein the measuring instrument comprises an optical microscope or scanning electron microscope.

3. The method according to claim 2, wherein for each of the measuring steps, the parameter is calculated in each case and compared with the respective limiting value.

4. The method according to claim 3, wherein for the measuring step of the alignment, the measured data obtained in this measuring step includes a digital image, the computing rule for calculating the value of the relevant parameter includes the comparison of the digital image with a reference image.

5. The method according to claim 3, wherein for the measuring step of the detection of the at least one pattern, the measured data obtained includes a digital image, the computing rule for calculating the value of the relevant parameter includes the comparison of the digital image with a reference image.

6. The method according to claim 3, wherein for the measuring step of aligning the lens system, the measured data obtained includes a measuring curve, the computing rule for calculating the value of the parameter relating to the measuring step includes the comparison of the measuring curve with a reference curve.

7. The method according to claim 3, wherein the measuring step of the characteristic dimension is carried out with the aid of at least two measurements of the at least one pattern, the computing rule of the parameter relating to the pattern width measuring step includes the comparison of a first measuring curve of a first measurement with a second measuring curve of a second measurement.

8. The method according to claim 1, wherein in the case of a plurality of parameters, the computing and control unit calculates one quality parameter the quality parameter representing the quality of the measurement from the calculated parameters, the quality parameter being compared with a prescribed quality limiting value, a warning signal being generated as a function of the comparison.

9. The method according to claim 8, wherein for the measuring step of the alignment, the measured data obtained in this measuring step includes a digital image, the computing rule for calculating the value of the relevant parameter includes the comparison of the digital image with a reference image.

10. The method according to claim 8, wherein for the measuring step of the detection of the at least one pattern, the measured data obtained includes a digital image, the computing rule for calculating the value of the relevant parameter includes the comparison of the digital image with a reference image.

11. The method according to claim 8, wherein for the measuring step of aligning the lens system, the measured data obtained includes a measuring curve, the computing rule for calculating the value of the parameter relating to the measuring step includes the comparison of the measuring curve with a reference curve.

12. The method according to claim 8, wherein the measuring step of the characteristic dimension is carried out with the aid of at least two measurements of the at least one pattern, the computing rule of the parameter relating to the pattern width measuring step includes the comparison of a first measuring curve of a first measurement with a second measuring curve of a second measurement.

13. The method according to claim 1, wherein the disc-shaped object is a semiconductor wafer, a mask, or a reticule or a flat panel display.

14. The method according to claim 1, wherein the measuring step is repeated for a multiplicity of disc-shaped objects, the value of the parameter for the respective measuring step is stored in a database, and a trend analysis is carried out for the parameter over the multiplicity of the respectively stored values.

* * * * *

UNITED STATES PATENT AND TRADEMARK OFFICE
CERTIFICATE OF CORRECTION

PATENT NO. : 6,980,304 B2
APPLICATION NO. : 10/802728
DATED : December 27, 2005
INVENTOR(S) : Oliver Broermann et al.

It is certified that error appears in the above-identified patent and that said Letters Patent is hereby corrected as shown below:

Claims 4-14 should read:

4. The method according to claim 1, wherein in the case of a plurality of parameters, the computing and control unit calculates one quality parameter the quality parameter representing the quality of the measurement from the calculated parameters, the quality parameter being compared with a prescribed quality limiting value, a warning signal being generated as a function of the comparison.

5. The method according to claim 3, wherein for the measuring step of the alignment, the measured data obtained in this measuring step includes a digital image, the computing rule for calculating the value of the relevant parameter includes the comparison of the digital image with a reference image.

6. The method according to claim 3, wherein for the measuring step of the detection of the at least one pattern, the measured data obtained includes a digital image, the computing rule for calculating the value of the relevant parameter includes the comparison of the digital image with a reference image.

7. The method according to claim 3, wherein for the measuring step of aligning the lens system, the measured data obtained includes a measuring curve, the computing rule for calculating the value of the parameter relating to the measuring step includes the comparison of the measuring curve with a reference curve.

8. The method according to claim 3, wherein the measuring step of the characteristic dimension is carried out with the aid of at least two measurements of the at least one pattern, the computing rule of the parameter relating to the pattern width measuring step includes the comparison of a first measuring curve of a first measurement with a second measuring curve of a second measurement.

9. The method according to claim 1, wherein the disc-shaped object is a semiconductor wafer, a mask, or a reticule or a flat panel display.

10. The method according to claim 1, wherein the measuring step is repeated for a multiplicity of disc-shaped objects, the value of the parameter for the respective measuring step is stored in a database, and a trend analysis is carried out for the parameter over the multiplicity of the respectively stored values.

UNITED STATES PATENT AND TRADEMARK OFFICE
CERTIFICATE OF CORRECTION

PATENT NO. : 6,980,304 B2
APPLICATION NO. : 10/802728
DATED : December 27, 2005
INVENTOR(S) : Oliver Broermann et al.

It is certified that error appears in the above-identified patent and that said Letters Patent is hereby corrected as shown below:

11. The method according to claim 4, wherein for the measuring step of the alignment, the measured data obtained in this measuring step includes a digital image, the computing rule for calculating the value of the relevant parameter includes the comparison of the digital image with a reference image.

12. The method according to claim 4, wherein for the measuring step of the detection of the at least one pattern, the measured data obtained includes a digital image, the computing rule for calculating the value of the relevant parameter includes the comparison of the digital image with a reference image.

13. The method according to claim 4, wherein for the measuring step of aligning the lens system, the measured data obtained includes a measuring curve, the computing rule for calculating the value of the parameter relating to the measuring step includes the comparison of the measuring curve with a reference curve.

14. The method according to claim 4, wherein the measuring step of the characteristic dimension is carried out with the aid of at least two measurements of the at least one pattern, the computing rule of the parameter relating to the pattern width measuring step includes the comparison of a first measuring curve of a first measurement with a second measuring curve of a second measurement.

Signed and Sealed this

Twenty-seventh Day of February, 2007

JON W. DUDAS
*Director of the United States Patent and Trademark Office*